United States Patent [19]

Lizzi et al.

[11] 4,350,917

[45] Sep. 21, 1982

[54] FREQUENCY-CONTROLLED SCANNING OF ULTRASONIC BEAMS

[75] Inventors: Frederic L. Lizzi, Tenafly, N.J.; Kurt W. Weil, New York, N.Y.

[73] Assignee: Riverside Research Institute, New York, N.Y.

[21] Appl. No.: 157,417

[22] Filed: Jun. 9, 1980

[51] Int. Cl.[3] .......................... H03J 3/28; H03H 9/40; A61B 10/00

[52] U.S. Cl. .................................... 310/320; 310/335; 310/369; 128/660; 333/186; 367/157

[58] Field of Search ............... 310/319, 320, 326, 329, 310/335, 334, 340, 367, 371, 369; 333/141-147, 186, 187, 193-196; 128/660, 661, 682; 367/157, 8, 153, 155

[56] References Cited

U.S. PATENT DOCUMENTS

| | | | |
|---|---|---|---|
| 2,485,722 | 1/1945 | Erwin | 171/327 |
| 3,179,823 | 4/1965 | Nesh | 310/8.4 |
| 3,470,395 | 9/1969 | Moffatt | 333/186 |
| 3,569,750 | 3/1971 | Beaver | 310/9.5 |
| 3,798,474 | 3/1974 | Cassand et al. | 310/9.6 |
| 3,939,467 | 2/1976 | Cook et al. | 340/8 R |
| 3,958,559 | 5/1976 | Glenn et al. | 310/335 |
| 3,987,320 | 10/1976 | Merhar | 310/369 |
| 4,075,516 | 2/1978 | Hattori et al. | 310/334 |
| 4,123,681 | 10/1978 | Barlow | 310/322 |
| 4,155,259 | 5/1979 | Engeler | 128/660 |
| 4,259,649 | 3/1981 | de Klerk | 333/147 |

OTHER PUBLICATIONS

Coquin et al., "Wide-Band Acoustooptic Deflectors Using Acoustic Beam Steering", IEEE, PG-S & U, vol. SU-17, Jan. 1970, pp. 34-40.

*Primary Examiner*—J. D. Miller
*Assistant Examiner*—D. L. Rebsch
*Attorney, Agent, or Firm*—Brumbaugh, Graves, Donohue & Raymond

[57] ABSTRACT

An ultrasonic wave transducer is formed from a body of piezoelectric material having nonuniform thickness. Each location on the transducer is resonant at a different frequency according to the thickness at that point. By changing the frequency of the applied excitation signal, the origin and direction of the radiation can be altered.

27 Claims, 9 Drawing Figures

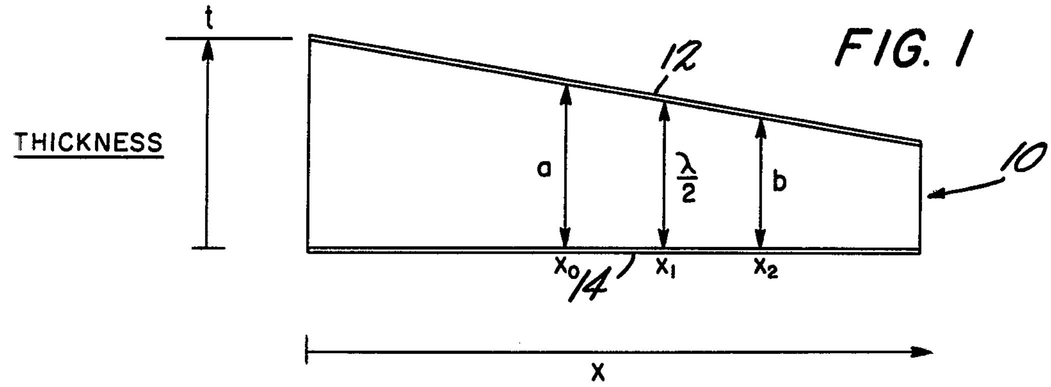
FIG. 1
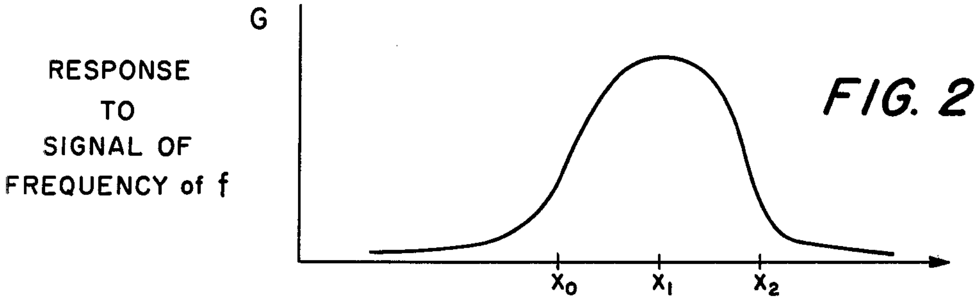
FIG. 2
FIG. 3
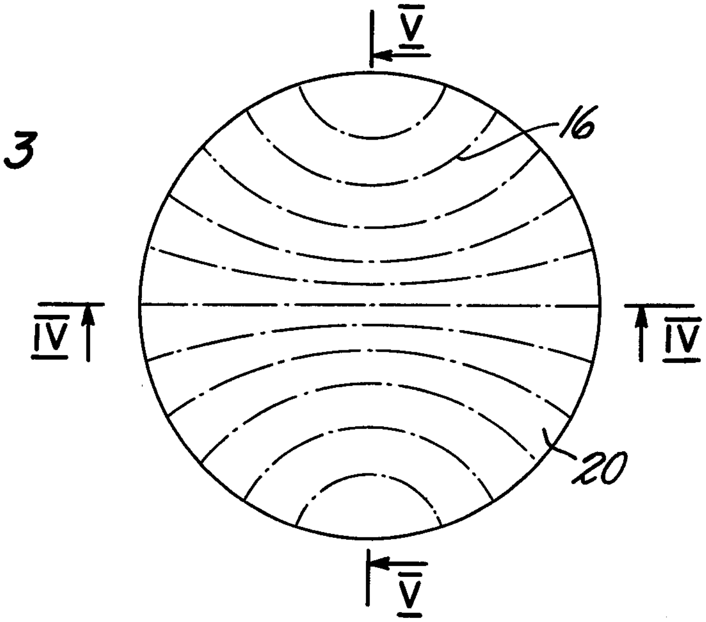
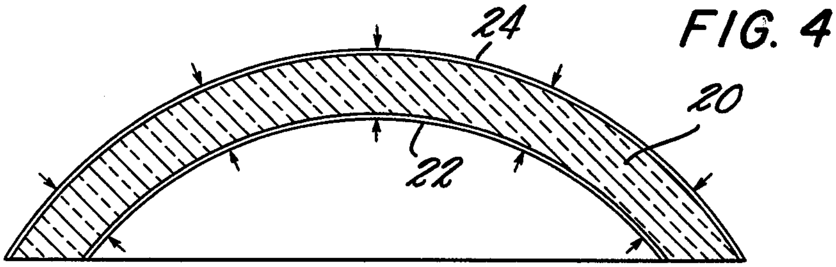
FIG. 4

FREQUENCY-CONTROLLED SCANNING OF ULTRASONIC BEAMS

BACKGROUND OF THE INVENTION

1. Field of the Invention

This invention relates to a piezoelectric transducer for converting electrical energy into ultrasonic wave energy.

2. Description of the Prior Art

Several examples of piezoelectric transducers are known in the prior art. In connection with such transducers it is known generally that the transducer operates over a range of frequencies adjacent to its "resonant" frequency, which is a function of the thickness of the transducer body and the type of material. U.S. Pat. No. 3,179,823 to Nesh describes a transducer having a wedge-shaped body, which, because of its varying thickness is resonant over a broad band of frequencies. The device is primarily intended to absorb and detect ambient vibratory energy in missiles and rockets. Energy is received from a direction normal to one of the flat surfaces 5 or 6, regardless of the frequency. Hence, the transducer has fixed, unidirectional radiation and reception patterns.

The transducer disclosed in U.S. Pat. No. 3,937,467 to Cook et al. is useful in sonar applications. "Teeth-like" projections of varying lengths give the transducer its broadbanded response. The radiation pattern shown in FIG. 15 spans approximately 180° in the horizontal plane over the entire frequency range. Although a curved surface is described in FIGS. 5 and 6, the reference does not attribute special directional characteristics to this configuration.

SUMMARY OF THE INVENTION

As mentioned above, the transducers known in the prior art have generally fixed radiation patterns. The present invention relates to transducers and systems wherein the direction of the radiation pattern can be electronically changed by varying the frequency of the electrical signal applied to the piezoelectric transducer.

In accordance with the present invention, the transducer's piezoelectric element is nonuniform in thickness and resonant over a range of frequencies determined by its maximum and minimum thickness. While the element may assume almost any shape, depending upon the desired variation of radiation direction, a spherical shell section of piezoelectric material is described herein as an advantageous embodiment. Since the ultrasonic waves are generally radiated in a direction normal to the radiation emitting surface of the element, a spherical element facilitates angular changes in the propagation direction of the radiated beam.

This invention is suitable for use in equipment for providing rapid ultrasonic (pulse-echo) visualization of moving body structures such as the heart, since the invention will enable such equipment to provide cross-sections B-scan at very high frame rates (e.g. above 60 frames/second).

Another feature of the spherical-shaped transducer is that it allows a large angular field-of-view from a limited spatial "window". This is useful in body scan equipment wherein ultrasonic rays must be directed to pass through the intercostal spaces between the ribs to examine the heart.

Directional scanning may be enhanced by creating thickness tapers with special patterns to provide the desired scan path. For instance, if the spherical shell is tapered along one arcuate path, there would be a series of imaginary contour lines of constant thickness running across the surface of the shell. An excitation signal at a particular frequency within the transducer's operating frequency band will excite the transducer in a region surrounding one such contour line. In another arrangement, the shell is tapered in a series of declining ramps running in a zig-zag or other path along the inner surface of the shell, the shell thickness at any given point along the path of the taper being unique. When excited by a single frequency signal, only a small zone surrounding the point of corresponding thickness will radiate energy. If the frequency is varied continuously, the emitted beam pattern will change its angular orientation in a like, continuous fashion.

To achieve the scanning operation mentioned above, a voltage-controlled oscillator is most useful. The oscillator can provide a signal having a continuously varied frequency during a selected time period. As the frequency changes, the surface area segment of the transducer which is excited is continuously changed. By choosing a rage of frequencies that corresponds to the thickness range of the transducer, every section of the device can be excited so that a scanning ultrasonic beam can be generated.

When the transducer has air on one side, and a fluid or fluid-like medium on the other side, most of the energy supplied to the transducer will radiate into the fluid medium.

For a better understanding of the present invention and other objects thereof, reference is made to the following description, taken in conjunction with the accompanying drawings, and its scope will be pointed out in the appended claims.

BRIEF DESCRIPTION OF THE DRAWINGS

FIG. 1 is a side view of a prior art transducer having nonuniform thickness;

FIG. 2 is a graph showing the response of the FIG. 1 transducer to a signal of frequency f;

FIG. 3 shows a plan view of a spherical shell transducer in accordance with the present invention;

FIGS. 4 and 5 are central sectional views of the transducer of FIG. 3;

DESCRIPTION OF THE PREFERRED EMBODIMENT

Figure 5:
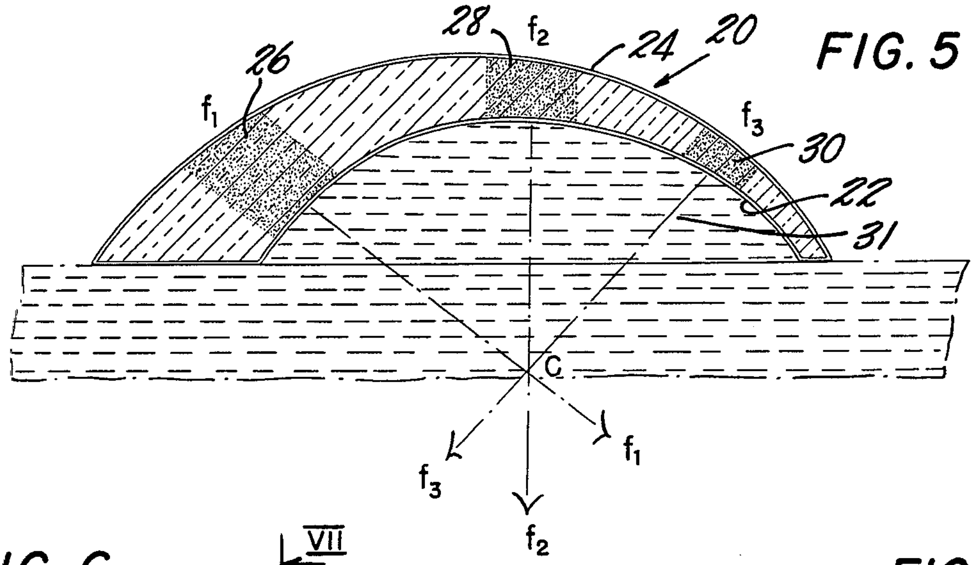

Referring generally to FIG. 1 there is shown a side view of a piezoelectric transducer having a nonuniform thickness in the direction indicated by t. In the drawing of FIG. 1, the thickness of transducer 10 varies linearly along its length in the X direction. Typically, transducer 10 is a body of piezoelectric material such as lithium niobate, quartz, or lead zirconate titanate. The upper and lower surfaces 12 and 14 of the body, as viewed in FIG. 1, are clad with a conductive material, and the body can be caused to vibrate by applying an alternating electric voltage between the upper and lower conductive cladding. Because of the piezoelectric characteristics of the crystal the applied voltage causes the crystal to expand and contract at the frequency of the applied voltage, and thereby transmit acoustic waves from the metal clad surfaces.

Those familiar with the art will recognize that the body 10 will vibrate with enhanced amplitude of vibration for applied signal frequencies at which the transducer thickness corresponds to a half-wavelength or an odd integral multiple of a half-wavelength. For these conditions the body vibration resonates and causes an improved impedance match between the input electrical signals and the radiation of the transducer, thereby increasing the percentage of applied electrical energy transmitted as acoustic waves.

In an arrangement such as illustrated in FIG. 1, wherein the thickness t of the transducer body varies along the X direction of the transducer, there will occur a localized resonant vibration of the transducer for each frequency of applied electrical signal. Accordingly, a transducer having tapered thickness will radiate acoustic waves primarily from an area corresponding to a transducer thickness of approximately a half-wavelength or an odd integral multiple of a half-wavelength. The amplitude characteristic of such localized vibration is illustrated for a particular selected frequency corresponding to an acoustic wavelength $\lambda$ in the material of the transducer body by the graph of FIG. 2. While prior art workers in the field have made use of a tapered transducer body thickness for the purposes of achieving broad-band operation, none have made use of the fact that the radiation from a tapered body is localized in the region surrounding the resonant thickness at the applied frequency. The present invention makes use of this phenomena in order to achieve steering of the radiated acoustic beams.

Referring to FIGS. 3 to 5 there is shown a preferred embodiment of the present invention consisting of a piezoelectric body 20 formed in the shape of a spherical shell. The shell has inner and outer curved surfaces 22, 24 both of which are spherical, and both of which are clad with a metal coating, functioning as electrodes. The metal coating is generally gold, silver or nichrome and has a thickness which is small in terms of acoustic wavelengths. The inner spherical surface has a smaller radius of curvature than the outer spherical surface and the center of curvature of .the spherical surface are displaced from each other along a direction corresponding to section V—V, thereby to achieve a tapering of the thickness of the spherical shell. Because of the tapered thickness of the spherical shell, the transducer has a region of response to applied signals which changes according to the frequency of the applied signals. As illustrated in FIG. 5, signals at a lower frequency $f_1$ cause a resonating of the spherical shell in a region 26 having a relatively thick dimension between the two spherical surfaces. At an intermediate frequency $f_2$ the body resonates at an area 28 approximately centered on the shell. At a higher frequency $f_3$ the shell resonates at a thinner portion indicated by 30 in FIG. 5. A two inch diameter portion of a shell having inner and outer surface radii of approximately 2 to 2.5 inches, and having thickness ranging from approximately 0.1 to 0.15 inches, made from lead zirconate titanate-type material was found to resonate in the frequency range of 800 kHz to 500 kHz. In order to avoid conditions wherein one part of the body resonates at the fundamental half-wave thickness, and another part resonates at an odd integral multiple of a half-wave, such as three half-waves, it is usually necessary to restrict the thickness variation, and hence the frequency variation to less than three-to-one.

Radiation from the spherical surfaces of the shell is primarily from surfaces having an adjacent medium whose acoustic impedance has a value reasonably close to that of the transducer material. In the arrangement illustrated in FIG. 5, the outer spherical surface borders on air, which has a very low acoustic impedance. The inner spherical surface borders on water 31 or other fluid-like material that has a higher acoustic impedance than air. As a result, the shell radiates acoustic wave signals primarily from the inner surface of the spherical shell in the region of resonant vibration. Thus, the inner surface of the shell forms a radiation aperture, and radiation emanates from different regions of the aperture in different directions according to the frequency of supplied electrical energy.

In the FIG. 3 drawing, lines of generally constant thickness are shown schematically on the spherical shell as contours 16. These contours approximately correspond to lines of latitude for either one of the two spheres forming the surfaces of the spherical shell. The lines of constant thickness have a progression along a central path through which the FIG. 5 cross section is taken, which comprises a circumference of longitude. Since the shell has constant thickness along each line 16, the areas surrounding each of these lines will be resonant and will radiate for applied signals having a frequency corresponding to a half-wavelength or an odd integral multiple of half-wavelength at the thicknesses of the contour. Since the resonant surface area is curved in the angular coordinate transverse to the longitudinal scanning direction, the beam will have a converging and then diverging shape in this coordinate, allowing penetration of the beam through a small opening, for example, between ribs in a body scanning device. As the frequency of the applied signals is varied, the region of acoustic radiation will move across the shell surface in the direction of the line of longitude, and the angular direction of the resulting sonic radiation will change.

The transducer shown in FIGS. 3 and 5 was tested by pointing the transducer upward through a water column towards an air-water interface and examining the beam as it caused localized elevations in the water surface. It was also used with a Schlieren system to delineate beam orientation. A transducer, having a diameter, d, of two inches was backed by air, and the radiation was directed into water. Angular beam excursions of $\pm 15$ degrees were achieved by stepping the excitation frequency through the frequency range 1.5 MHz to 2.5 MHz. When pulse-type waveforms (20 $\mu$sec pulse duration) were applied to the transducer, echoes were received from a metallic plate placed in front of the transducer, whenever the ultrasonic beam was normal to the surface of the plate.

Figure 6:
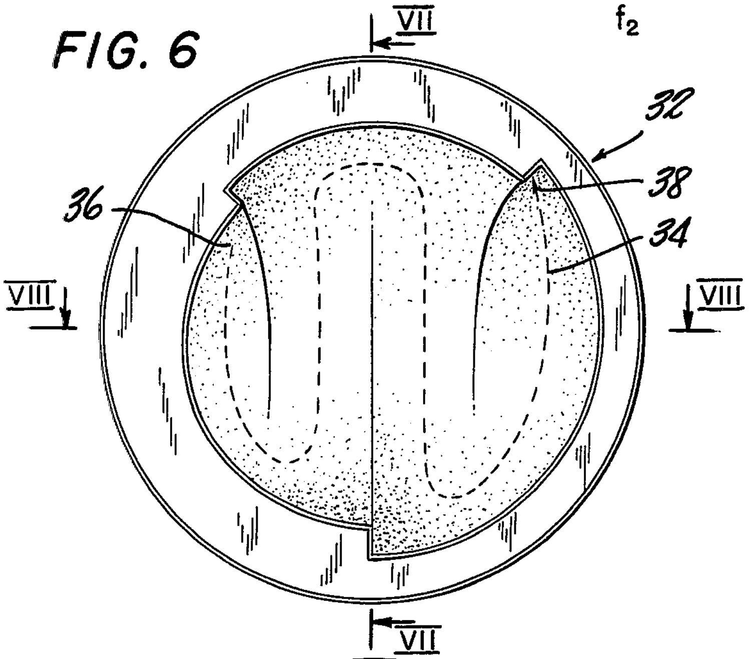
FIG. 6 shows a plan view of a shell transducer in accordance with the invention having a zig-zag path of continuously increasing thickness.
Figure 7:
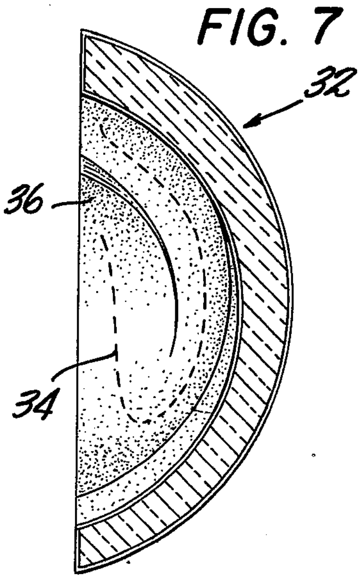
FIGS. 7 and 8 are central cross-sectional views of the FIG. 6 transducer.
Figure 8:
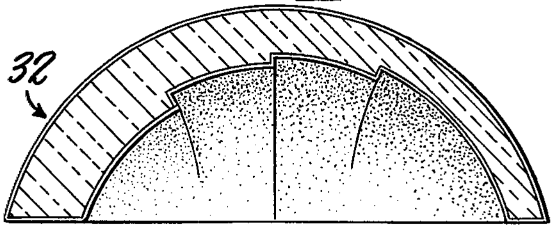

In the embodiment of FIGS. 3 to 5, beam movement is possible in only one angular coordinate. To provide full control of acoustic radiation direction a transducer that can scan in two angular coordinates would be helpful. FIGS. 6 to 8 illustrate a transducer capable of moving a beam through two angular coordinates in a zig-zag scan pattern. FIG. 6 shows a plan view of the transducer 32 having "zig-zag" path 34 of decreasing shell thickness. This path is in actuality a series of tapered ramps decreasing in thickness as the path proceeds from one end 36 to the other end 38. FIGS. 7 and 8 are cross sectional views of transducer 32 showing the tapers.

When swept frequency electrical signals are supplied to the metal clad inner and outer surfaces of transducer 32, the direction of the radiated acoustic waves will vary in a zig-zag raster like pattern in space. Those skilled in the art will recognize that other, variable thickness configurations are possible to achieve multi-coordinate angular beam movement. Thus, it is possible to provide spiral path of increasing or decreasing thickness and have a corresponding spiral-like acoustic beam scan with varying frequency signals. Another possibility is discrete steps of different thickness rather than the tapered path, with application of discrete frequencies.

A voltage-controlled oscillator performs well with the transducers illustrated in FIGS. 3 and 6, to provide an electrical signal with a time-varying frequency, thus changing the point of resonance on the transducer surface in a continuous fashion. As the frequency of the generator output changes, either in a decreasing or increasing fashion, the zone of resonance will move along the path, thus scanning the entire surface. Alternatively, the frequency can be changed from one value to another without using intermediate values to change the direction of the radiated beam in a non-continuous manner suitable for random access applications.

Figure 9:
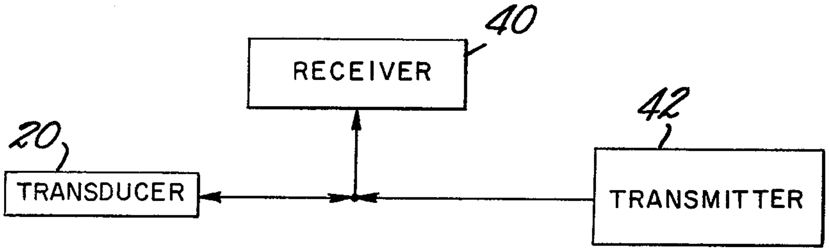
FIG. 9 illustrates an ultrasonic radiating system in accordance with the present invention.

FIG. 9 shows a system incorporating a transducer, a transmitter, and a receiver. This system may operate in one of at least two operating modes for determining the direction of origin for acoustic echo signals. In a first mode, a brief, broad-band pulse is applied to the transducer to cause the transducer to resonate simultaneously in virtually all surface areas. In this operational mode, the frequency of the radiated acoustic energy will vary as a function of the angular direction of acoustic radiation. For example, radiation in the direction indicated as $f_1$ in FIG. 5 will have a low frequency while radiation in the direction $f_3$ of FIG. 5 will have a high frequency. Echoes from targets within the region into which the transducer radiates can be discriminated, as to direction, according to the frequency of the returned echo. This can be done by using a bank of band-pass filters, the center-frequency of each filter corresponding to a distinct acoustic beam direction.

In an alternate method of using the system of the present invention, the frequency of the signal applied to the transducer can be changed, for example from pulse to pulse, so that a relatively narrow beam of radiation is radiated in response to each narrow-band pulse and in a direction of radiation that is determined according to the frequency of the pulse.

While the present invention is described with particular reference to systems and transducers which are arranged for transmitting acoustic signals, those familiar with the art will recognize that such transducers are entirely reciprocal and that the same principles apply to the use of a transducer for transmitting as well as for receiving acoustic signals. Accordingly, the present specification and claims are intended to apply equally to transducers which are used for receiving acoustic wave energy signals from a region as well as to transducers for transmitting acoustical signals into the region.

Although certain specific embodiments have been shown and described, it will be obvious to one skilled in the art that many modifications are possible. The invention, therefore, is not intended to be restricted to the exact showing of the drawings and description thereof, but is considered to include reasonable and obvious equivalents.

We claim:

1. A transducer, responsive to supplied electrical signals within a selected frequency range, for radiating said signals as ultrasonic waves, comprising a body of material having selected acoustic characteristics and having at least a first curved surface, a second opposite surface and a thickness between said surfaces, which thickness is different for different selected locations on said curved surface, said thickness being a resonant thickness in said material at said different locations for different frequencies in said frequency range, whereby when said electrical signals are applied to said body, said body resonates between said surfaces at locations on said curved surface according to the frequency spectrum of said electrical signals, and said body radiates ultrasonic waves from said curved surface at said locations.

2. A transducer as set forth in claim 1 wherein said material is piezoelectric.

3. A transducer as set forth in claim 2 wherein said curved surface and said opposite surface are metal clad, and said electrical signals are applied to said body by said cladding.

4. A transducer as set forth in claim 1 wherein said second surface is curved.

5. A transducer as set forth in claim 1 wherein all cross-sections of said curved surface are curved.

6. A transducer as set forth in claim 4 wherein one of said curved surfaces is convex and other of said curved surfaces is concave, whereby said body comprises a portion of a curved shell.

7. A transducer as set forth in claim 1 wherein said second surface interfaces with air.

8. A transducer as set forth in claim 7 wherein a selected material having acoustic characteristics simulating fluid is adjacent said first surface, whereby said body radiates into said selected material.

9. A transducer as set forth in claim 1 wherein said selected frequency range encompasses a range wherein the highest frequency is less than three times the lowest frequency.

10. A transducer as set forth in claim 9 wherein said thickness varies over a range where the greatest thickness is less than three times the smallest thickness.

11. A transducer as set forth in claim 4 wherein said surfaces are spherical.

12. A transducer as set forth in claim 1 wherein said transducer has contour lines of constant thickness, said lines being transverse to a selected path on said surface, each thickness being resonant at a particular frequency in said frequency range, whereby application of a signal at a selected frequency causes said body to radiate ultrasonic waves from all areas over said line of constant thickness corresponding to said selected frequency, and said body radiates ultrasonic waves in a pattern determined partially by the length of said line, and whereby variation of said selected frequency causes movement of said areas of radiation in a direction corresponding to said selected path.

13. A transducer as specified in claim 12 wherein said selected path is a line formed by the intersection of a plane and said curved surface.

14. A transducer as specified in claim 12 wherein said selected path is a zig-zag line.

15. A transducer as specified in claim 13 wherein said first curved surface is a first sphere, wherein said second surface is a second sphere with an offset center from said first sphere, wherein said lines comprise approximately lines of latitude, and wherein said path is a circumference of longitude.

16. A transducer as set forth in claim 6 wherein said shell is divided into a plurality of sections of constant thickness and each of said sections is resonant at a corresponding frequency of applied signals.

17. In a transducer for radiating ultrasonic waves in response to supplied electrical signals wherein there is provided a body of material having selected acoustic characteristics, the improvement wherein said body has at least one curved surface and an opposite surface, and wherein the thickness between said surfaces is different for different selected locations on said curved surface, and resonant at different locations for different frequencies of applied signals, whereby when said electrical signals are applied to said body, said body resonates at a location on said curved surface according to the frequency of said electrical signals, and said body radiates ultrasonic waves from said curved surface at said location.

18. Apparatus for radiating sonic waves into a medium comprising a transducer element of selected acoustic characteristics having at least one curved surface, an opposite surface, and a thickness therebetween, said thickness being different at different selected locations on said curved surface, and means connected to said transducer for generating and supplying electrical signals at various frequencies within a selected frequency range;

whereby, when a signal at a particular frequency is applied to said transducer element, a location having a thickness that is resonant at said frequency will radiate sonic waves at said location.

19. Apparatus as set forth in claim 18, wherein said transducer element is a body of piezoelectric material.

20. Apparatus as set forth in claim 19, wherein said curved surface and said opposite surface are metal clad, and said electrical signals are applied to said body by said cladding.

21. Apparatus as set forth in claim 18, wherein said generating means is a variable frequency generator.

22. Apparatus as set forth in claim 21, wherein said variable frequency generator is a voltage-controlled oscillator arranged to sequentially generate a plurality of frequencies within said selected frequency resonating each said location on said curved surface in a desired sequence.

23. Apparatus as set forth in claim 18, wherein said selected frequency range encompasses a range wherein the highest frequency is less than three times the lowest freeuqncy.

24. Apparatus as set forth in claim 18 wherein said generating means is arranged to provide a broad-band signal having a plurality of simultaneous frequency components within said selected frequency range to simultaneously resonate a corresponding plurality of locations on said curved surface.

25. In a system for radiating ultrasonic waves from a transducer into an unbounded region of space, wherein a signal generator supplies electrical signals which are radiated as ultrasonic waves by a transducer, the improvement wherein said signal generator generates signals of different frequencies and said transducer radiates said signals as ultrasonic waves in different directions for different signal frequencies.

26. Apparatus as specified in claim 25 wherein said transducer includes a body having tapered thickness whereby said body resonates at different locations for said different frequencies.

27. Apparatus for radiating acoustic signals, comprising a radiating aperture, resposive to acoustic signals of different frequencies, for radiating said signals into different directions in an unbounded region of space from said aperture, the direction of radiation being determined by the frequency of said signal, and means for supplying acoustic signals to said radiating aperture.

* * * * *